United States Patent
Suzuki et al.

(10) Patent No.: US 9,636,264 B2
(45) Date of Patent: May 2, 2017

(54) ABSORBENT ARTICLE

(75) Inventors: Migaku Suzuki, Tokyo (JP); Yoshio Hirai, Tokyo (JP)

(73) Assignee: DAIO PAPER CORPORATION, Shikokuchuo-shi (JP)

(*) Notice: Subject to any disclaimer, the term of this patent is extended or adjusted under 35 U.S.C. 154(b) by 22 days.

(21) Appl. No.: 14/363,032

(22) PCT Filed: Mar. 12, 2012

(86) PCT No.: PCT/JP2012/056297
§ 371 (c)(1),
(2), (4) Date: Jun. 5, 2014

(87) PCT Pub. No.: WO2013/088751
PCT Pub. Date: Jun. 20, 2013

(65) Prior Publication Data
US 2015/0005731 A1    Jan. 1, 2015

(30) Foreign Application Priority Data
Dec. 13, 2011 (JP) .................................. 2011-271939

(51) Int. Cl.
*A61F 13/49* (2006.01)
*A61F 13/491* (2006.01)
(Continued)

(52) U.S. Cl.
CPC .. *A61F 13/49413* (2013.01); *A61F 13/49446* (2013.01); *A61F 13/511* (2013.01);
(Continued)

(58) Field of Classification Search
CPC .......... A61F 13/49406; A61F 13/49413; A61F 13/4942; A61F 2013/49433;
(Continued)

(56) References Cited

U.S. PATENT DOCUMENTS 4,892,528 A * 1/1990 Suzuki et al. ............ 604/385.27
6,152,908 A * 11/2000 Widlund et al. ......... 604/385.19
(Continued)

FOREIGN PATENT DOCUMENTS

AU         675943      2/1997
GB      2 287 393 A    9/1995
(Continued)

OTHER PUBLICATIONS

Office Action issued Japanese Patent Application No. 2012-513397 dated Jun. 19, 2012 (with translation).
(Continued)

*Primary Examiner* — Peter S Vasat
(74) *Attorney, Agent, or Firm* — Oliff PLC

(57) ABSTRACT

An absorbent article has a basic functionality of a skin contact sheet present and configured on the surface of an absorber such that it rises therefrom, in which no positional displacement occurs at a crotch part and which effectively avoids contact between a wearer's skin and urine/feces. The absorbent article has: a leak preventer in sheet form; an absorber arranged above the leak preventer and capable of absorbing a bodily fluid in at least one layer; a skin contact member arranged above the absorber, between a front part of the leak preventer and a rear part of the leak preventer, and that makes contact with a wearer's skin and is spaced apart from the absorber at a time of use; and a connecting unit that couples a part of the skin contact member corresponding to a crotch part of the wearer with the absorber at the time of use.

20 Claims, 14 Drawing Sheets

(51) Int. Cl.
*A61F 13/495* (2006.01)
*A61F 13/494* (2006.01)
*A61F 13/511* (2006.01)

(52) U.S. Cl.
CPC ............... *A61F 2013/49493* (2013.01); *A61F 2013/51195* (2013.01)

(58) Field of Classification Search
CPC ........ A61F 2013/4944; A61F 13/49446; A61F 13/49453
USPC ............ 604/385.24, 385.25, 385.26, 385.27, 604/385.28
See application file for complete search history.

(56) References Cited

U.S. PATENT DOCUMENTS

| | | | |
|---|---|---|---|
| 7,842,019 | B2 | 11/2010 | Sugiyama et al. |
| 2006/0241557 | A1 | 10/2006 | Moriya et al. |
| 2009/0005752 | A1* | 1/2009 | Suzuki et al. ......... 604/385.101 |

FOREIGN PATENT DOCUMENTS

| | | |
|---|---|---|
| JP | U-06-007725 | 2/1994 |
| JP | A-2002-011044 | 1/2002 |
| JP | A-2002-143217 | 5/2002 |
| JP | A-2002-204811 | 7/2002 |
| JP | A-2002-345887 | 12/2002 |
| JP | A-2007-236911 | 9/2007 |
| JP | 2008-086428 A | 4/2008 |
| JP | 2009-219744 A | 10/2009 |
| KR | 10-2008-0098005 A | 11/2008 |

OTHER PUBLICATIONS

Written Opinion of the International Searching Authority issued in International Patent Application No. PCT/JP2012/056297 mailed May 15, 2012 (with translation).
Aug. 12, 2015 Office Action isued in Korean Patent Application No. KR 10-2014-7015935.
Aug. 4, 2015 European Extended Search Report issued in European Patent Application No. 12857855.6.
May 15, 2012 International Search Report issued in International Application No. PCT/JP2012/056297.

* cited by examiner (A)

(B)

(A)

(B)

(A)

(B)

(A)

(B)

(A)

(B)

(A)

(B)

(A)

(B)

(A)

(B)

(A)

(B)

ABSORBENT ARTICLE

FIELD OF THE INVENTION

The present invention relates to an absorbent article.

BACKGROUND ART

Absorbent articles such as paper diapers (for infants and adults), sanitary napkins, incontinence articles, training pants or the like are articles that absorb bodily fluids such as urine excreted from a wearer by means of an absorber that makes use of a super absorbent polymer (hereinafter referred to as "SAP").

Conventionally, it is known to provide a skin contact sheet which is made to abut the wearer in a closely-attached condition by a resilient member and which has an opening for the permeation of feces (see Patent Documents 1 to 3).

PRIOR ART REFERENCES

Patent Documents

Patent Document 1: Japanese Laid-Open Patent Application No. 2002-011044

Patent Document 2: Japanese Laid-Open Patent Application No. 2002-143217

Patent Document 3: Japanese Laid-Open Patent Application No. 2002-204811

SUMMARY OF THE INVENTION

Problems to be Solved by the Invention

The inventors of the present application capture the recent technical trends regarding absorbent articles, including the absorbent articles described in Patent Documents 1 to 3, as below.

In the structural design of an absorbent article, the conventional basic structure has been configured by a top sheet, a back sheet and an absorber interposed therebetween. However, recently, emphasis has been placed on considering the arrangement of the components in a more three-dimensional (3D) manner and designs are changing so as to allow the respective parts to have corresponding functions. Table 1 below organizes and describes this idea by making use of an infant's diaper (medium and large sizes).

TABLE 1

| 3D (X, Y, Z) projections and functional differentiation regarding structural design of an infant's diaper | | |
|---|---|---|
| (Z-direction) Outermost surface ↓ Rearmost surface | Outermost surface: skin contact sheet Absorbent surface: urine contact sheet, feces contact sheet Absorbent body: thinned SAP/pulp mixture, SAP sheet Leakage prevention surface: urine barrier sheet, feces barrier sheet | |
| (X-direction) Diaper edge part and Inseam part clearance | Diaper edge part gathers (ILG) and the interval therebetween Prevention of a side leakage from the absorbent surface Intervals between the tops of the gather: 70-100 mm Inseam part clearance Intervals of skin seals for prevention of a leakage along the skin: 20-30 mm | |
| (Y-direction) Front end edge part ↓ Rear end edge part | Near front end part: front end seal, front urine pocket Front half part: urine reception and collection part, urine absorption part Central part: narrowing part, crotch part urine-feces separation part Rear half part: urine absorption part, feces reception and holding part Near rear end part: rear end seal, rear feces pocket | Front body Inseam part Back body |

(A) Regarding Z-Direction Arrangement (Arrangement from the Outermost Surface that Makes Contact with a Wearer's Skin to a Leak Preventer at the Rearmost Surface)

Conventionally, the outermost surface has been the top sheet and it had a configuration in which a wearer's skin was in constant contact with excreted urine and feces since both urine and feces were received thereon.

Recently, as described in Table 1 above, it has been proposed to arrange a skin contact sheet above the outermost surface such that it rises from the top surface of the absorber and is constantly in close contact with the skin, and such that contact with excreted urine and feces is avoided, and to obtain a configuration in which a urine/feces contact sheet, an absorber, and a urine/feces barrier sheet above the rear surface are arranged in this order from the top (see Patent Documents 1 to 3 above).

However, according to the inventors' review, this newly-introduced skin contact sheet is only fixed at the front and rear end parts. Since there are no other fixing points, it has a fatal flaw to the effect that, when it is used, a positional displacement occurs in the lateral direction and the front-and-back direction, in particular, at the important central crotch part and, thus, the position thereof is not stable.

(B) Regarding X-Direction Arrangement (Arrangement from Both End Parts in the Width Direction of the Absorbent Article to the Center Thereof)

Generally, by means of gusset gathers bonded to the back sheet on both sides and inner leg gather (ILG) that rise in the vicinity of both edges of the absorber, urine and feces that flow along the surface of the absorber are blocked at the sides and thus, side leakage is prevented.

However, despite the fact that the intervals between the tops of the ILG arranged on both sides are approximately the same (typically, 70-100 mm) at all of an abdominal part (front side), a crotch part (central part) and a back part (rear side), when in use, at the crotch part, due to its narrow interval (typically, 20-30 mm), the skin contact sheet is compressed in a considerably deformed manner and, thus, it makes contact with a perineal area of the wearer in a non-uniform manner. Accordingly, this still constitutes a major cause of leakage.

(C) Regarding Y-Direction Arrangement (Arrangement from a Front End Edge Part to a Rear End Edge Part in the Length Direction of the Absorbent Article)

There are five parts when the Y direction is classified based on their functions. However, in a more rough classification, there are three parts including a front body which corresponds to the abdominal part side of the wearer, a crotch part which corresponds to the part in the vicinity of the perineal area of the wearer and a rear body which corresponds to the back part side of the wearer (see Table 1). The design of particular importance in a diaper is the design of the crotch part where an outlet for excreting urine and feces is close thereto and, further, is in a narrowed condition.

The object of the present invention is to provide an absorbent article which has a basic functionality of a skin contact sheet that is present and configured above the surface of an absorber such that it rises therefrom, in which no positional displacement occurs at a crotch part and which effectively avoids contact between a wearer's skin and urine/feces.

Means for Solving the Problems

As result of diligently conducting research so as achieve the object set forth above, the present inventors have found that positional displacement of a skin contact member at the perineal area may be prevented and, thus, the contact of the excreted urine/feces with a wearer's skin may be effectively prevented by providing above an absorber, between a front part of a leak preventer and a rear part of the leak preventer, a skin contact member that makes contact with a wearer's skin at the time of use, by allowing an absorber and such skin contact member to be spaced apart from each other, and by further providing a connecting unit that couples a part of the skin contact member corresponding to a crotch part of the wearer at the time of use and the absorber, and then completed the present invention.

Namely, the present invention provides the following (1) to (16):

(1) An absorbent article including: a leak preventer in sheet form; an absorber that is arranged above the leak preventer and is capable of absorbing a bodily fluid in at least one layer; a skin contact member that is arranged above the absorber, between a front part of the leak preventer and a rear part of the leak preventer, and that makes contact with a wearer's skin and is spaced apart from the absorber at the time of use; and a connecting unit that couples a part of the skin contact member corresponding to a crotch part of the wearer with the absorber at the time of use.

(2) The absorbent article according to section (1) above, wherein the skin contact member is a sheet having a urine permeation opening in a front body part and a feces permeation opening in a rear body part.

(3) The absorbent article according to section (2) above, wherein a part of the connecting unit that is forward of a part that couples to the skin contact member hangs down to a lower side of the urine permeation opening.

(4) The absorbent article according to section (2) or (3) above, wherein the connecting unit covers at least part of the absorber in an area from the crotch part to a rear end part.

(5) The absorbent article according to section (2) or (3) above, wherein right and left end parts of the connecting unit extend to right and left end parts of the leak preventer.

(6) The absorbent article according to section (1) above, wherein the skin contact member has two belt-like members, on the right and left sides, that extend in a front-rear direction, and the connecting unit connects the two belt-like members to each other at a part of the skin contact member corresponding to the crotch part of the wearer.

(7) The absorbent article according to section (6) above, wherein a part of the connecting unit that is forward of a part that couples to the skin contact member hangs down to a lower side of the urine permeation opening.

(8) The absorbent article according to section (6) or (7) above, wherein the connecting unit covers at least part of the absorber in an area from the crotch part to a rear end part.

(9) The absorbent article according to section (6) or (7) above, wherein right and left end parts of the connecting unit extend up to right and left end parts of the leak preventer.

(10) The absorbent article according to section (1) above, wherein the skin contact member includes: two belt-like members, on the right and left sides, that extend in a front-rear direction; and a hanging member that hangs down from the belt-like members, and the connecting unit connects the two belt-like members to each other at a part of the skin contact member corresponding to the crotch part of the wearer.

(11) The absorbent article according to section (10) above, wherein a part of the connecting unit that is forward of a part that couples to the skin contact member hangs down to a lower side of the urine permeation opening.

(12) The absorbent article according to section (10) or (11) above, wherein the connecting unit covers at least part of the absorber in an area from the crotch part to a rear end part.

(13) The absorbent article according to section (10) or (11) above, wherein right and left end parts of the connecting unit extend to right and left end parts of the leak preventer.

(14) The absorbent article according to any of sections (1) to (13) above, wherein the absorber contains a super absorbent polymer.

(15) The absorbent article according to any one of sections (1) to (14) above, further comprising a pair of right and left inner leg gathers provided further outside from a position where the skin contact member is present in the lateral direction.

(16) The absorbent article according to any one of sections (1) to (15) above, further comprising a pair of right and left outer leg gathers provided further outside from a position where the skin contact member is present in the lateral direction.

Effect of the Invention

The absorbent article according to the present invention is capable of effectively preventing contact of the excreted urine/feces with a wearer's skin.

BRIEF DESCRIPTIONS OF THE DRAWINGS

Figure 7:
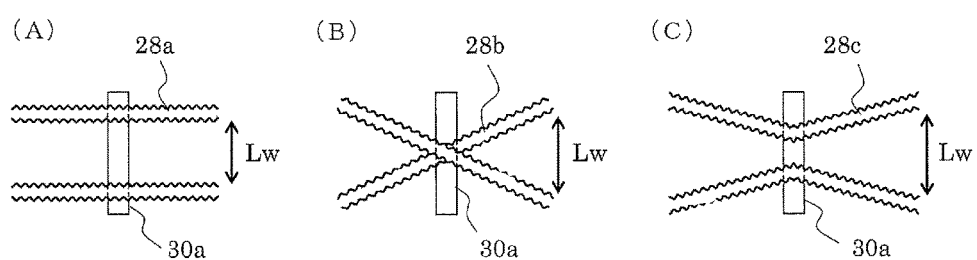

FIG. 7 contains schematic plan views illustrating various arrangement examples of a skin contact member having two belt-like members used for the absorbent article according to the present invention.

Figure 8:
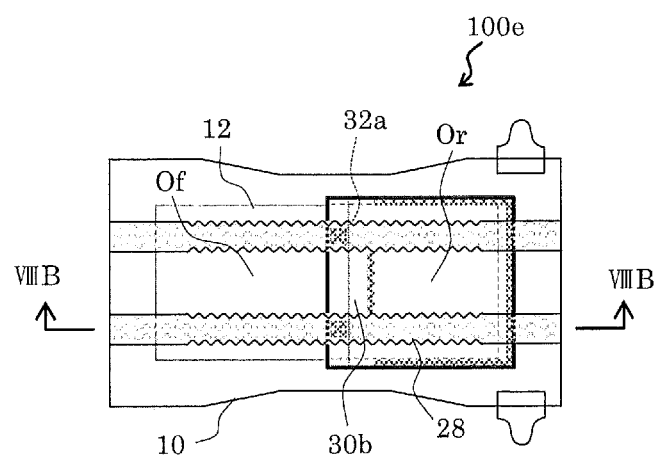
Figure 8:
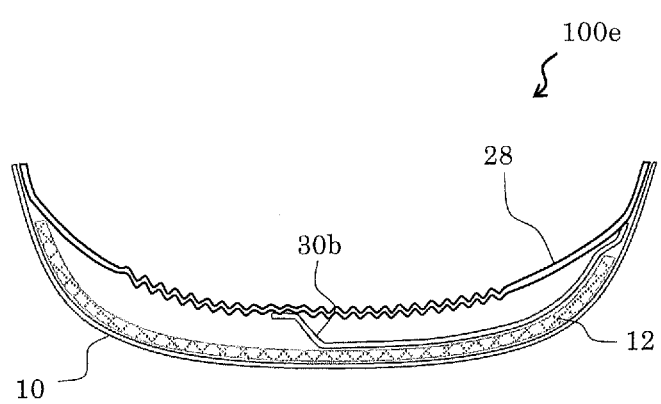

FIG. 8 is a schematic diagram illustrating another example of an absorbent article according to the present invention.

Figure 9:
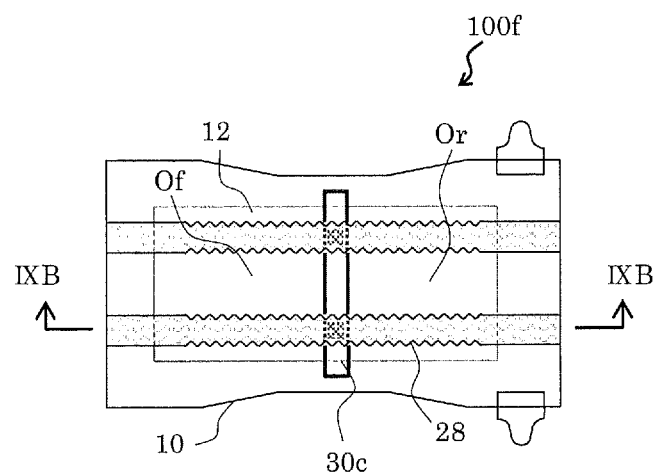
Figure 9:
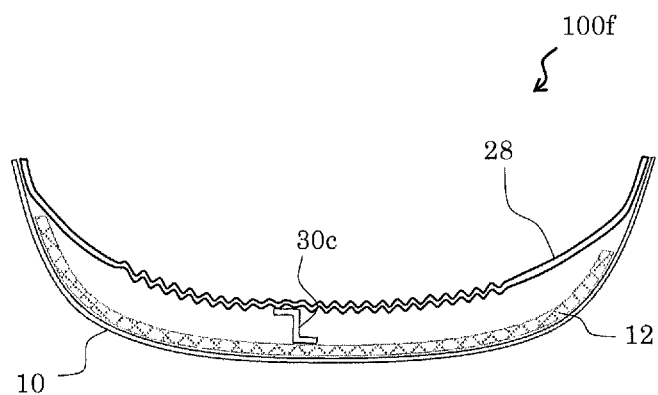

FIG. 9 is a schematic diagram illustrating another example of an absorbent article according to the present invention.

Figure 10:
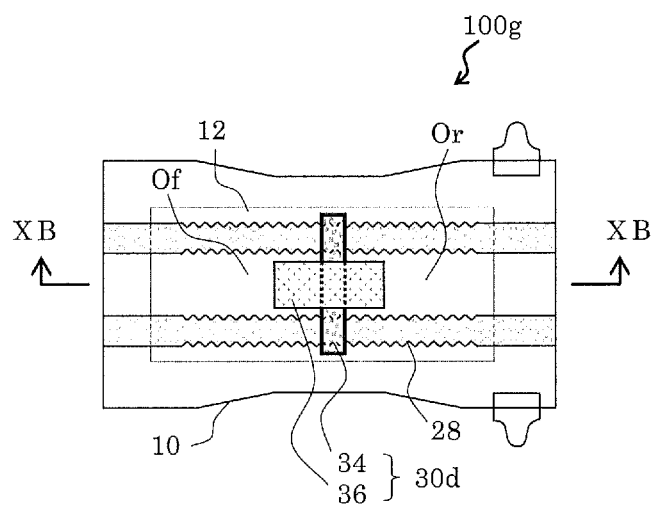

FIG. 10 is a schematic diagram illustrating another example of an absorbent article according to the present invention.

Figure 11:
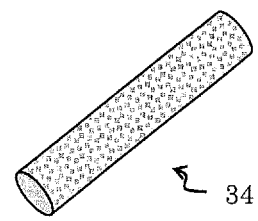

FIG. 11 is a schematic perspective view of connecting member 34.

Figure 12:
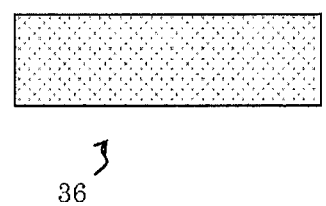

FIG. 12 is a schematic plan view of connecting member 36.

Figure 13:
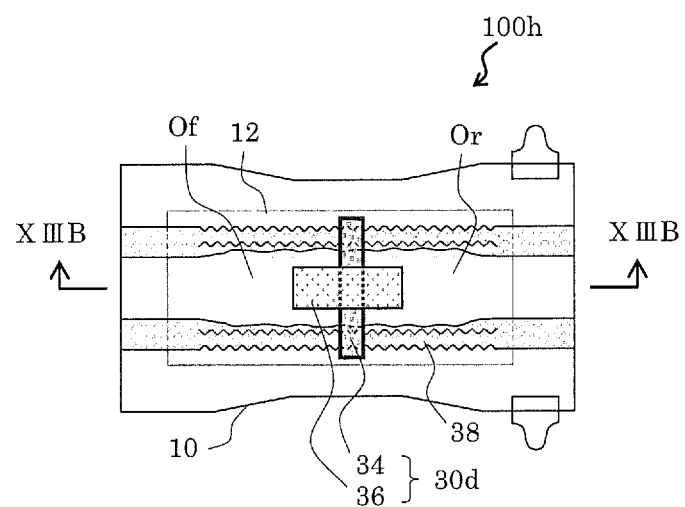
Figure 13:
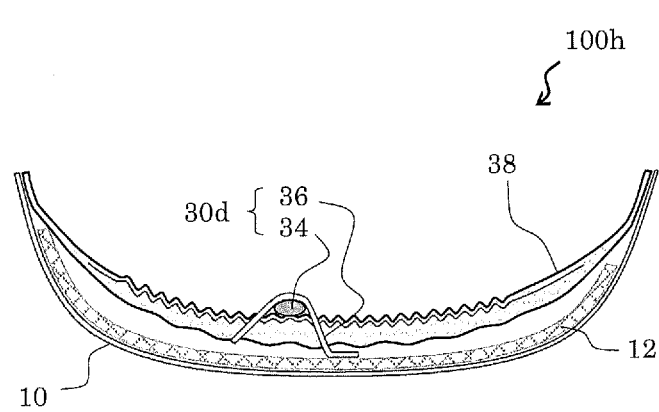

FIG. 13 is a schematic diagram illustrating another example of an absorbent article according to the present invention.

Figure 14:
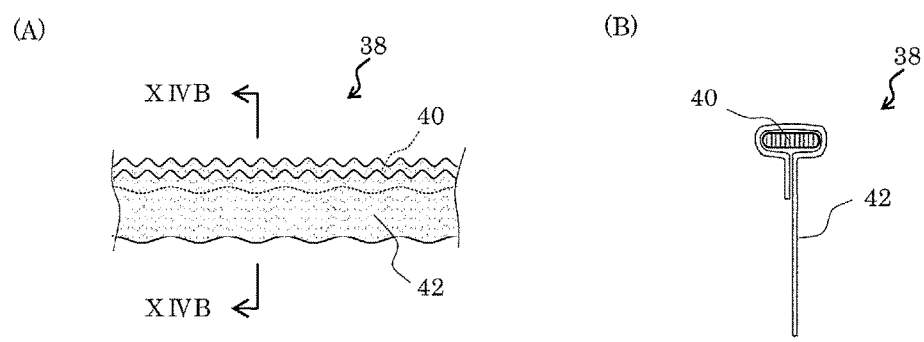

FIG. 14 is a schematic diagram of skin contact member 38.

Figure 15:
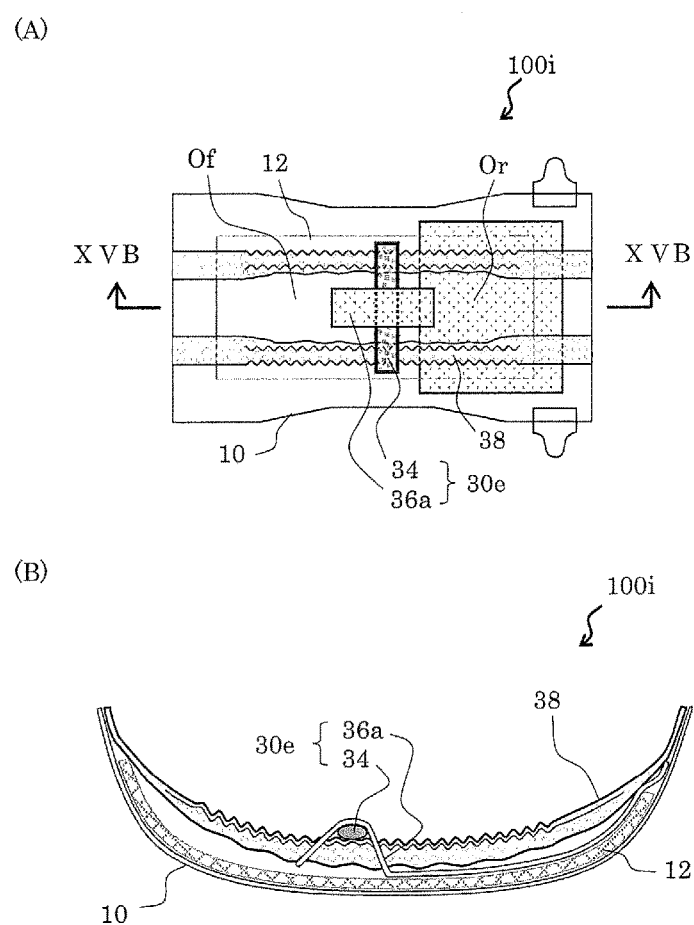

FIG. 15 is a schematic diagram illustrating another example of an absorbent article according to the present invention.

Figure 16:
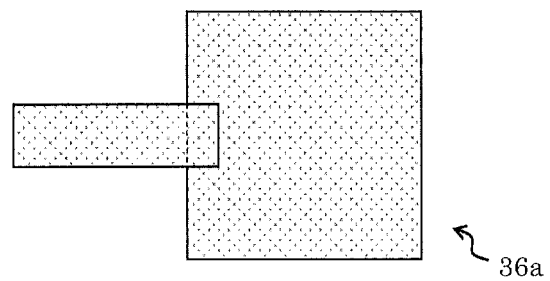

FIG. 16 is a schematic plan view of connecting member 36a.

Figure 17:
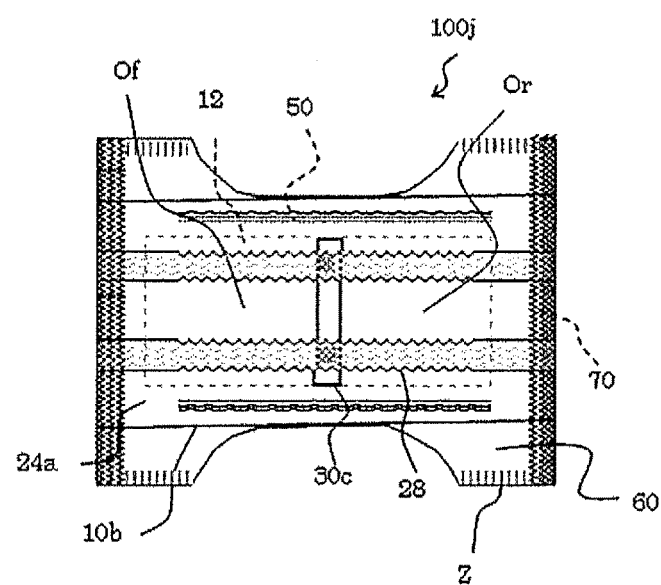
Figure 17:
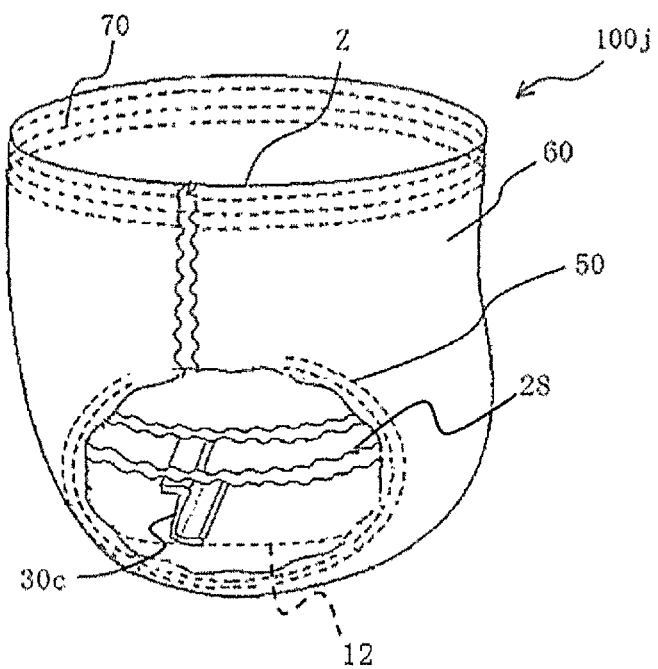

FIG. 17 is a schematic diagram illustrating another example of an absorbent article according to the present invention.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article, etc. is illustrated such that it is positioned on the left side of the corresponding drawing. In the respective longitudinal end face views and longitudinal sectional views among the attached drawings, the front side of the absorbent article, etc. is illustrated such that it is positioned on the left side of the corresponding drawing. In addition, regarding the dimensions of various parts, they are represented based on medium and large sizes of an infant's diaper and when an adult's diaper is illustrated, the dimensions are also represented based on medium and large sizes of an adult's diaper.

Figure 1:
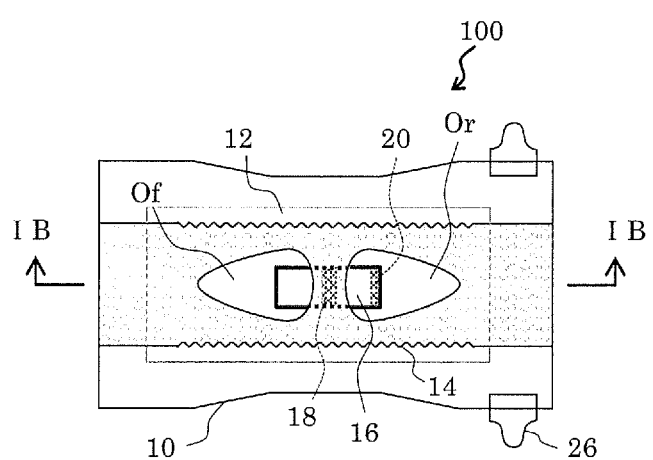
FIG. 1 is a schematic diagram illustrating an example of an absorbent article according to the present invention.
Figure 1:
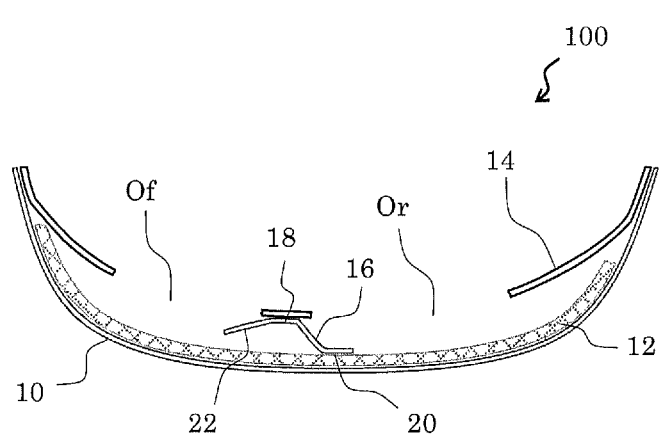

FIG. 1 is a schematic diagram illustrating an example of an absorbent article according to the present invention. FIG. 1(A) is a plan view thereof and FIG. 1(B) is a longitudinal end face view taken along line IB-IB shown in FIG. 1(A).

Absorbent article 100 according to the present invention illustrated in FIG. 1 basically includes: leak preventer 10 in sheet form; at least one layer of absorber 12 that is arranged above leak preventer 10 and that contains a super absorbent polymer so as to absorb bodily fluid; skin contact member 14 that is arranged above absorber 12, between a front part of leak preventer 10 and a rear part of leak preventer 10, and that makes contact with a wearer's skin and that is spaced apart from absorber 12 at the time of use; and connecting unit 16 that couples a part of skin contact member 14 corresponding to a crotch part of the wearer at the time of use to absorber 12.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may be preferably used.

In addition, when the above-described resin film is used, a multilayered sheet of such film and a non-woven fabric may be used in order to improve the texture and appearance. In this case, a spunbond (SB) or thermalbond non-woven fabric having a relatively low basis weight (for example, a spot-bond non-woven fabric made of PP) or the like may preferably be used as the non-woven fabric.

Moreover, a multilayered sheet of such resin film and an absorber in sheet form, which is described below, may also be used.

Further, a high water-resistance non-woven fabric may also be used. Examples of such high water-resistance non-woven fabric include an SMS non-woven fabric having a degree of a water resistance of 100 mmH$_2$O or more and an SB non-woven fabric in which pores in a microfiber web are filled with microfibrillated cellulose (MFC) or wax so as to provide such fabric with water resistance. In this case, a high water-resistance non-woven fabric may be used alone or may also be used as a multilayered sheet of the film and such high water-resistance non-woven fabric.

Leak preventer 10 may be configured from a plurality of members.

Leak preventer 10 is not particularly limited in terms of its shape, as long as it has a sheet form.

Absorber 12 used in the present invention is not particularly limited, as long as it is capable of absorbing bodily fluid, and any absorber used in publicly known conventional absorbent articles may be used. For example, powdery wooden pulp, a powdery absorber (such as raw SAP, etc.) and an absorber in sheet form may be used.

An absorber in sheet form excels in morphological stability and capability of SAP fall prevention, etc.

Among various types of absorber in sheet form, a super absorbent sheet containing 50 mass % or more, preferably 60 mass % or more, or more preferably 70 mass % or more of SAP is preferred. In addition, from the perspective of stability, etc. of the super absorbent sheet, the content of SAP therein is preferably 95 mass % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, crushed wooden pulp and SAP are mixed and a binder is added to shape the mixture into a sheet form and then a super absorbent sheet is obtained. As examples of a super absorbent sheet obtained through this process, NOVATHIN (US trademark) manufactured by Rayonier Inc. in the US and B-SAP manufactured by Oji Kinocloth Co., Ltd. are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorber Technology Institute is known.

Other examples of the super absorbent sheet include: a super absorbent sheet obtained through a process involving having a raised non-woven fabric carry a large amount of SAP and fixing the SAP with a hot melt binder, an emulsion binder, an aqueous fiber, or the like; a super absorbent sheet obtained through a process involving mixing fibrous SAP with a PET (polyethylene terephthalate) fiber and forming the mixture into a web; and an SAP sheet obtained by providing tissues above and below an SAP layer.

At least one layer of absorber 12 is arranged above leak preventer 10. Namely, absorber 12 may be comprised of one layer or two or more layers (multilayer).

In addition, absorber 12 may be arranged in a folded condition.

It should be noted that, in the present invention, the coupling between the absorber and a connecting unit refers to the coupling between the upper side surface of the absorber and the connecting unit when the absorber is exposed or the coupling between the upper side surface of an acquisition layer or top sheet and the connecting unit when such acquisition layer or top sheet attached to the absorber surface is present.

As shown in FIG. 1, skin contact member 14 is arranged above absorber 12 between a front part of leak preventer 10 and a rear part of leak preventer 10.

The configuration of skin contact member 14 is not particularly limited, so long as it makes contact with the wearer's skin and is spaced apart from absorber 12 at the time of use. For example, as shown in FIG. 1(B), skin contact member 14 may have a configuration in which the length of the two parts of skin contact member 14 which respectively couple with the front part and rear part of leak preventer 10 is smaller than the length of leak preventer 10 corresponding to those parts.

In addition, the skin contact member is preferably stretchable so as to facilitate constant contact with the wearer's skin. For providing stretchability, examples of implementation include configuring the skin contact member itself with a knit, a net, a non-woven fabric, or the like, made of a stretchable member such as a stretchable polyurethane filament, or the like, and bonding a stretchable member to each side edge of the skin contact member. More particularly, for example, as the skin contact sheet described in Patent Document 1, a skin contact sheet having a configuration in which an elastic member is bonded and in which such elastic member is stretched when in use and abuts the wearer's skin in a closely-attached condition may be used.

The skin contact member is not particularly limited in terms of its shape and, for example, a sheet-like, band-like, curtain-like and parallel-rail-like shape may be employed.

Preferably, the material configuring the skin contact member is low irritative, and the surface thereof should be smooth and soft and not become sticky to the skin even when sweat is absorbed, since the skin contact member will make direct contact with the wearer's skin when in use.

In particular, examples of the material configuring the skin contact member preferably include: a mesh made of filaments of, for example, PE, PP, PET, nylon, or the like; a non-woven fabric such as an air-through non-woven fabric, a spunmelt non-woven fabric and a spunlace non-woven fabric, which makes use of fine synthetic fibers (preferably 5 denier or less) as raw materials; a perforated processed article of the above-described non-woven fabric; and a ribbed processed article of the above-described non-woven fabric.

Since the skin contact sheet will make direct contact with the wearer's skin, the surface of these materials is preferably hydrophilic and, in particular, sweat-absorber. In particular, examples thereof include: a sheet where a surface-hydrophilization treatment is applied to a non-woven fabric configured from synthetic fibers; and a sheet having a two-layered configuration of a hydrophilic non-woven fabric at the top and a hydrophobic non-woven fabric at the bottom.

Skin contact member 14 illustrated in FIG. 1 is a sheet having urine permeation opening Of in the front body part and feces permeation opening Or in the rear body part.

By providing skin contact member 14 with such configuration having urine permeation opening Of and feces permeation opening Or, it is possible to broadly cover absorber 12 by parts other than these openings. Thus, absorber 12 and skin contact member 14 are generally spaced apart. However, even when absorber 12 deforms and approaches the wearer depending on his/her body position or the like, skin contact member 14 serves to reduce the area of the wearer's skin which is in direct contact with absorber 12.

In one of the preferred embodiments, the skin contact member has one or both of the urine permeation opening and the feces permeation opening as described above.

The urine permeation opening corresponds to an opening for passing urine excreted from the urethral meatus when the absorbent article according to the present invention is used as an absorbent article for females and the urine permeation opening accommodates a penis or a penis and testicles when the absorbent article according to the present invention is used as an absorbent article for males.

The shape of the urine permeation opening is not particularly limited, as long as it performs the above-described function. For example, as shown in FIG. 1(A), the front body of the skin contact member may be formed with a triangular notch with rounded angles. The shape of the notch is not particularly limited and a circular or rectangular notch may be formed in addition to the above. Instead of a notch, a slit may be provided in the skin contact member.

The feces permeation opening allows the feces excreted by the wearer to penetrate therethrough, and the feces are received on the absorber.

The shape of the feces permeation opening is not particularly limited, as long as it performs the above-described function. For example, as shown in FIG. 1(A), the rear body of the skin contact member may be formed with a triangular notch with rounded angles. The shape of the notch is not particularly limited and a circular or rectangular notch may be formed in addition to the above.

Examples of the embodiments of a skin contact member without a urine permeation opening and a feces permeation opening include an embodiment which is a sheet in which the front part and/or rear part of the skin contact member is/are deeply hollowed to the position where urine or feces will be excreted and an embodiment in which the skin contact member has a plurality of bands (for example, a total of two bands on both sides) and the position where urine or feces will be excreted corresponds to the gap between the bands.

Connecting unit 16 couples a part of skin contact member 14 corresponding to the crotch part of the wearer at the time of use with absorber 12. This will prevent the lateral positional displacement of skin contact member 14 at the time of use.

Figure 2:
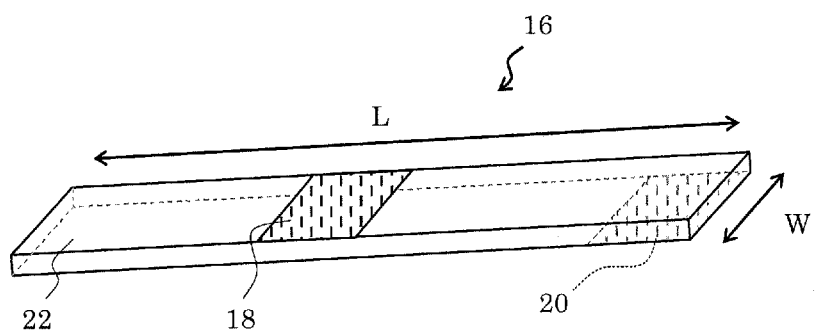
FIG. 2 is a schematic perspective view illustrating an example of a connecting unit.

FIG. 2 is a schematic perspective view illustrating an example of a connecting unit.

As shown in FIG. 2, connecting unit 16 is a rectangular sheet. Connecting unit 16 includes coupling part 18, which couples to the part of skin contact member 14 corresponding to the crotch part of the wearer at the time of use, and coupling part 20 that couples to absorber 12.

As shown in FIG. 1, connecting unit 16 couples to each of skin contact member 14 and absorber 12 with the corresponding coupling part 18 and coupling part 20.

The coupling method is not particularly limited and, for example, the coupling method may be achieved with an adhesive.

In addition, in FIG. 1, coupling part 18 of connecting unit 16 is coupled to the under surface of skin contact member 14; however, the present invention is not limited thereto. For example, the connecting unit may couple to the top surface of the part of the skin contact member corresponding to the crotch part of the wearer (see FIGS. 10, 13 and 15).

In connecting unit 16, hanging part 22, which is present forward of coupling part 18, forms a flow path when the urine excreted from the wearer transfers to absorber 12. In this way, when the part that is forward of the part of connecting unit 16 that couples to skin contact member 14 hangs down to the lower side of urine permeation opening Of, a smooth transfer of urine to absorber 12 is achieved and this is particularly useful when the absorbent article according to the present invention is intended for females.

The configuration of the connecting unit is not limited to the one illustrated in FIG. 2, as long as it couples the absorber and the skin contact member to each other. For example, connecting unit may have a sheet-shaped form, a belt-shaped and sheeted form, a net-shaped form, and a thread-shaped form.

A connecting unit in sheet form may be configured, for example, by one sheet, or by two or more sheets being superimposed on each other.

The connecting unit in sheet form preferably has a length in the front-rear direction (denoted with L in FIG. 2) of 60-120 mm and a width in the lateral direction (denoted with W in FIG. 2) of 30-100 mm.

As described above, according to absorbent article 100, skin contact member 14 makes contact with the wearer's skin and is spaced apart from absorber 12 at the time of use. Thus, it is possible to suppress the occurrence of discomfort due to the urine absorbed in absorber 12 or the urine that remains to be absorbed by absorber 12 making contact with the wearer's skin or the occurrence of staining due to the feces received on absorber 12 making contact with the wearer's skin.

In addition, as described above, according to absorbent article 100, the lateral positional displacement of skin contact member 14 (in particular, the lateral positional displacement at the crotch part) at the time of use can be prevented by connecting unit 16. Accordingly, it is possible to effectively prevent the occurrence of urine side leakage due to the gap formed by the skin contact member displacing from the perineal area at the time of use, the occurrence of wetting of the skin by the urine due to skin contact member 14 becoming wetted by the urine and the occurrence of staining on the buttocks due to the feces remaining on skin contact member 14.

It should be noted that, according to the present invention, it is preferable for the range of lateral direction movement of the connecting unit to be narrow. The range of front-rear direction movement thereof is controlled by the spacing (in the front-rear direction) between coupling part 18 and coupling part 20 and is preferably wide to a certain degree, from the perspective of keeping the wearer's skin and absorber 12 spaced apart.

The connecting unit preferably keeps a predetermined distance (for example, 10-20 mm) between the skin contact member and the absorber.

Absorbent article 100 according to the present invention illustrated in FIG. 1 can be specifically configured in the following manner.

For example, skin contact member 14 may be provided in the following manner.

First, both side ends of a PE/PP spunbond non-woven fabric (manufactured by, for example, Chisso Corporation) having a front-rear direction length of 450 mm, a lateral direction width of 90 mm and a basis weight of 13 g/m² are folded by 10 mm, and two urethane filaments (200 dtex) (manufactured by, for example, Du Pont-Toray Co., Ltd.) are bonded to the both folded side ends and placed thereon with an adhesive so as to provide both side ends with stretchability.

Subsequently, urine permeation opening Of and feces permeation opening Or are respectively formed in the front body and the rear body so that they are spaced apart by 10 mm and then, skin contact member 14 is obtained.

Then, under the condition where the obtained skin contact member 14 is stretched, its front end part and rear end part are respectively fixed to near a front end part and near a rear end part of leak preventer 10 through a hot melt process. When doing so, it is also possible to fix together the front ends and rear ends of skin contact member 14 and absorber 12 by enlarging the portion to be fixed to more than that shown in FIG. 1.

Further, when the front end part and rear end part of the leak preventer are covered with a member such as an acquisition layer or a top sheet (for example, when the absorber and the leak preventer are globally covered with a member such as an acquisition layer or a top sheet), it is possible to fix the skin contact member and the leak preventer via the covered members.

For example, connecting unit 16 may be provided in the following manner.

First, a TCF non-woven fabric (manufactured by, for example, Futamura Chemical Co., Ltd.) is laminated on the top surface of an elastomer net (35 mesh) (manufactured by, for example, Conwed Global Netting Solutions) to obtain connecting unit 16. Connecting unit 16 is, for example, formed in a belt-shaped and sheeted form having a front-rear direction length of 100 mm and a lateral direction width of 30 mm.

Coupling part 18 of the obtained connecting unit 16 is coupled to the under surface of the part of skin contact member 14 corresponding to the crotch part of the wearer and coupling part 20 thereof is coupled to the top surface of absorber 12. In this way, the spacing between the top surface of absorber 12 and the under surface of skin contact member 14 is easily kept at a predetermined distance (for example, approximately 15 mm).

The part of connecting unit 16 which is forward of coupling part 18 hangs down.

Hereinafter, other preferred embodiments of the skin contact member and the connecting unit in the absorbent article according to the present invention will be described.

Figure 3:
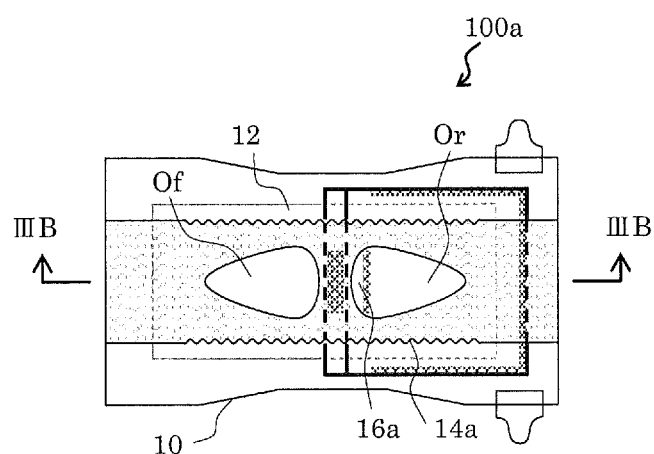
FIG. 3 is a schematic diagram illustrating another example of an absorbent article according to the present invention.
Figure 3:
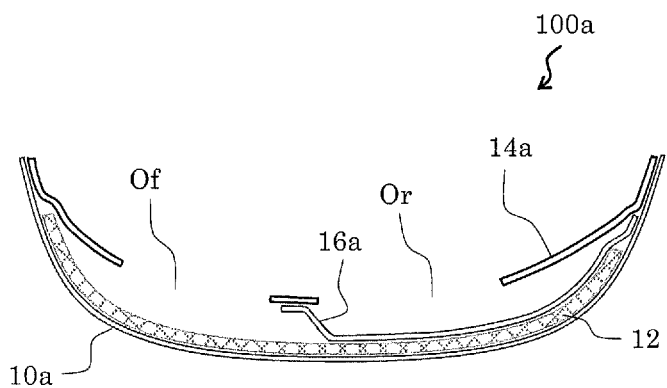

FIG. 3 is a schematic diagram illustrating another example of an absorbent article according to the present invention. FIG. 3(A) is a plan view thereof and FIG. 3(B) is a longitudinal end face view taken along line IIIB-IIIB shown in FIG. 3(A).

Absorbent article 100*a* shown in FIG. 3 is basically similar to absorbent article 100, except for connecting unit 16*a* having a configuration different from that of connecting unit 16.

The lateral direction width of connecting unit 16*a* is larger than that of absorber 12 and skin contact member 14*a*.

The central part of the front end part of connecting unit 16*a* couples to the under surface of the part of skin contact member 14*a* corresponding to the crotch part of the wearer. In addition, as will be described below, connecting unit 16*a* also couples to absorber 12, and thus, as with connecting unit 16, it is possible to prevent, at the time of use, the lateral positional displacement of skin contact member 14*a*. Further, as with the case of connecting unit 16, skin contact member 14*a* is movable within a certain range in the front-rear direction.

Further, a greater part of the rear side of connecting unit 16*a* covers, in the rear body, the entire top surface of absorber 12. The coupling between connecting unit 16*a* and absorber 12 may be made, in the part where contact is made therebetween, totally or only partially.

The rear side part of connecting unit 16*a* receives feces excreted from the wearer and penetrated through feces permeation opening Or.

According to the present embodiment, connecting unit 16*a* preferably couples to leak preventer 10 at its right and left side edge parts and its rear end part. In this way, absorber 12 is present, in the rear body, in the enclosed space formed by connecting unit 16*a* and leak preventer 10 and thus, when a liquid-impermeable or liquid-poorly-permeating material is used for connecting unit 16*a*, the leakage of urine absorbed by absorber 12 to the outside can be prevented. In addition, it is also possible to prevent the occurrence of problems such as the odor becoming strong due to the mixing of the feces received at the upper side of connecting unit 16*a* and the urine absorbed in absorber 12 at the under surface of connecting unit 16*a* and the easy occurrence of rashes.

Absorbent article 100*a* according to the present invention illustrated in FIG. 3 can be specifically configured in the following manner.

For example, skin contact member 14*a* may be provided in the following manner.

First, above a PP/SMS non-woven fabric (manufactured by, for example, Avgol) having a front-rear direction length of 450 mm, a lateral direction width of 70 mm and a basis weight of 13 g/m$^2$, a rayon spunlace non-woven fabric (manufactured by, for example, Daiwabo Rayon Co., Ltd.) having a basis weight of 20 g/cm$^2$, and also having a plurality of pores (with a diameter of approximately 1 mm) on the entire surface thereof, is superimposed, and, at the right and left side edge parts, two urethane filaments (200 dtex) (manufactured by, for example, Du Pont-Toray Co., Ltd.) are sandwiched, under a stretched condition, between the above two non-woven fabrics and bonded thereto by an adhesive so as to provide the right and left side edge parts with stretchability.

Subsequently, urine permeation opening Of and feces permeation opening Or are respectively provided and formed in the front body and the rear body so that they are spaced apart by 10 mm and then, skin contact member 14*a* is obtained.

Further, under the condition where the obtained skin contact member 14*a* is stretched, its front end part and rear end part are respectively fixed to near a front end part and near a rear end part of leak preventer 10 through a hot melt process.

For example, connecting unit 16*a* may be provided in the following manner.

First, a laminated body of a PE film, having leakage prevention properties, and an SMS non-woven fabric, is used as connecting unit 16*a*. Connecting unit 16*a* are, for example, formed in a wide belt-shaped and sheeted form having a front-rear direction length of 250 mm and a lateral direction width of 140 mm.

The front end part of connecting unit 16*a* is coupled to the under surface of the part of skin contact member 14*a* corresponding to the crotch part of the wearer and a greater part of the rear side thereof covers the top surface of absorber 12 and is coupled to skin contact member 14*a* having a spacing of 30 mm provided in the rearward direction from the coupling part between skin contact member 14*a* and the front end part. Further, the right and left side edge parts and the rear end part of connecting part 16*a* having a spacing of 30 mm provided in the rearward direction from the coupling part of skin contact member 14*a*, couple to leak preventer 10.

Figure 4:
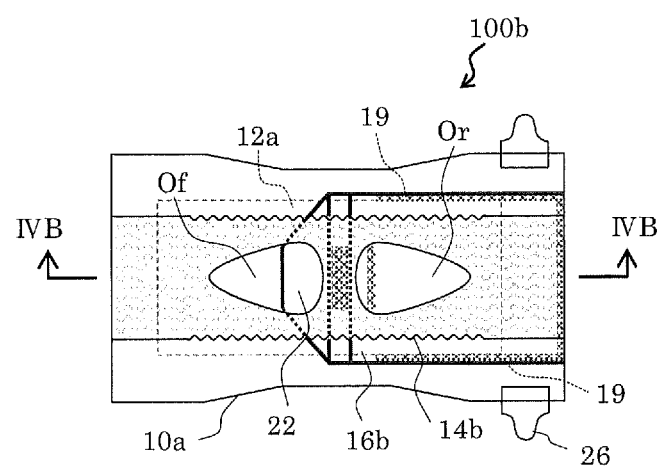
FIG. 4 is a schematic diagram illustrating another example of an absorbent article according to the present invention.
Figure 4:
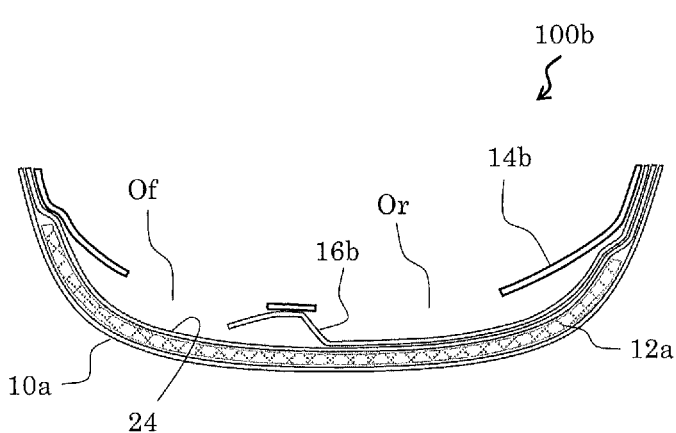

FIG. 4 is a schematic diagram illustrating another example of an absorbent article according to the present invention. FIG. 4(A) is a plan view thereof and FIG. 4(B) is a longitudinal end face view taken along line IVB-IVB shown in FIG. 4(A).

Absorbent article 100*b* shown in FIG. 4 is basically similar to absorbent article 100, except for connecting unit 16*b* having a configuration different from that of connecting unit 16.

As with connecting unit 16, connecting unit 16*b* couples to the under surface of the part of skin contact member 14*b* corresponding to the crotch part of the wearer and has a hanging part that hangs down in a linguiform forward of such coupling part. In addition, as with connecting unit 16*a*, connecting unit 16*b* gradually lowers and makes contact with absorber 12*a* as it extends in the rearward direction in the rear part from such coupling part, and covers the entire surface of absorber 12*a*. Connecting unit 16*b* couples to absorber 12*a* at the contact part with absorber 12*a*.

Connecting unit 16*b* couples to the rear end part of leak preventer 10*a* and also couples to the right and left side parts of leak preventer 10*a* at coupling part 19.

According to absorbent article 100*b*, top sheet 24 is provided on top of absorber 12 (it is provided under connecting unit 16*b* in the rear body). By having top sheet 24, even when the absorber makes contact with the wearer's skin, the stimulus thereof will be mitigated and the attachment of the SAP which has dropped out of the absorber to the skin will be prevented.

The top sheet is not particularly limited and, for example, any publicly-known conventional top sheet may be used.

Leak preventer 10a has detachable member 26, at each of the right and left side edge parts of the rear body, which has a binding tape that allows attachment to or detachment from the front body.

Absorbent article 100b can preferably be used for an infant's diaper or an adult's diaper.

Figure 5:
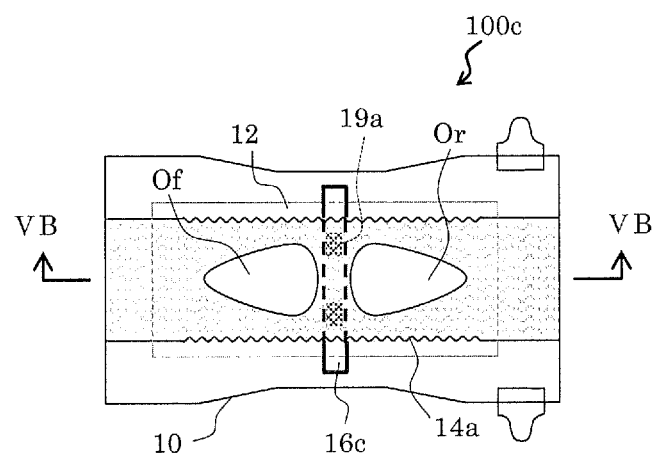
FIG. 5 is a schematic diagram illustrating another example of an absorbent article according to the present invention.
Figure 5:
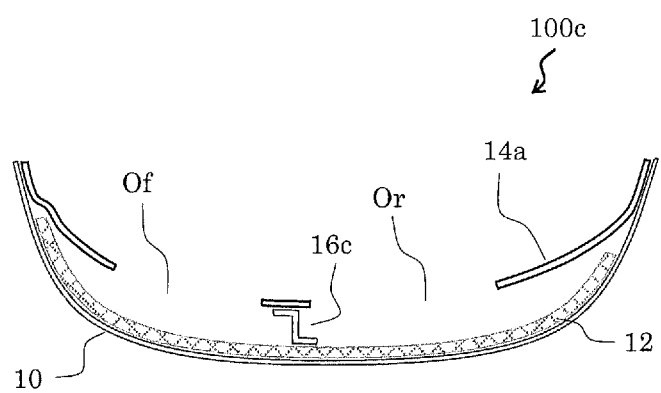

FIG. 5 is a schematic diagram illustrating another example of an absorbent article according to the present invention. FIG. 5(A) is a plan view thereof and FIG. 5(B) is a longitudinal end face view taken along line VB-VB shown in FIG. 5(A).

Absorbent article 100c shown in FIG. 5 is basically similar to absorbent article 100, except for connecting unit 16c having a configuration different from that of connecting unit 16.

As with connecting unit 16a, the front end part of connecting unit 16c couples to the under surface of the part of skin contact member 14a corresponding to the crotch part of the wearer. However, the rear end part thereof couples to the top surface of absorber 12, which is located substantially directly beneath the rear end part.

The right and left end parts of connecting unit 16c extend up to the right and left end parts of leak preventer 10, at the central part of absorbent article 100c. In this way, connecting unit 16c divides the internal space of leak preventer 10 into front and rear sections and, thus, it is possible to effectively prevent the urine excreted into the internal space of leak preventer 10 in the front body from transferring into the rear body and the feces excreted into the internal space of leak preventer 10 in the rear body from transferring into the front body. In particular, connecting unit 16c preferably has leakage prevention properties.

The coupling between the front end part of connecting unit 16c and the under surface of skin contact member 14a is made at two coupling parts 19a distributed to the right and left sides. In this way, the stretchability of the right and left edge parts of skin contact member 14a is not hindered.

Thus, since connecting unit 16c couples skin contact member 14a and absorber 12 at two locations, skin contact member 14a is substantially incapable of moving in the lateral direction; however, it is movable within a certain range in the front-rear direction. Accordingly, the part of skin contact member 14a corresponding to the crotch part of the wearer (i.e. the part between urine permeation opening Of and feces permeation opening Or) can be easily made in close attachment with the crotch part (perineal area) of the wearer.

Absorbent article 100c according to the present invention illustrated in FIG. 5 can be specifically configured in the following manner.

Skin contact member 14a may be provided in a similar manner to skin contact member 14a in absorbent article 100a illustrated in FIG. 3.

Connecting unit 16c may be provided by making use of a three-layered laminated body of, for example, a PP/SMS non-woven fabric, a PE film and a PP/SMS non-woven fabric.

Figure 6:
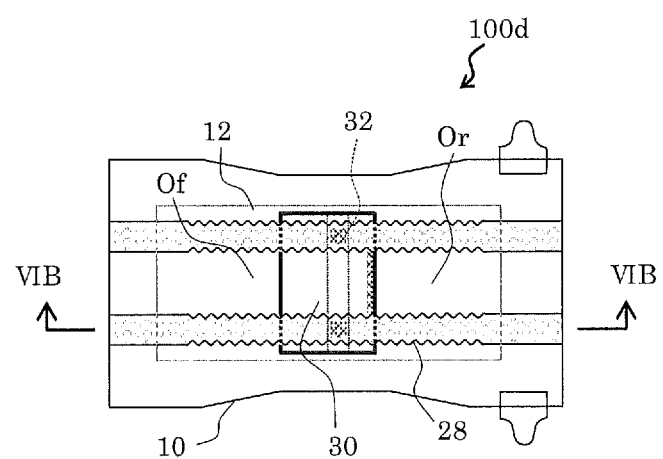
FIG. 6 is a schematic diagram illustrating another example of an absorbent article according to the present invention.
Figure 6:
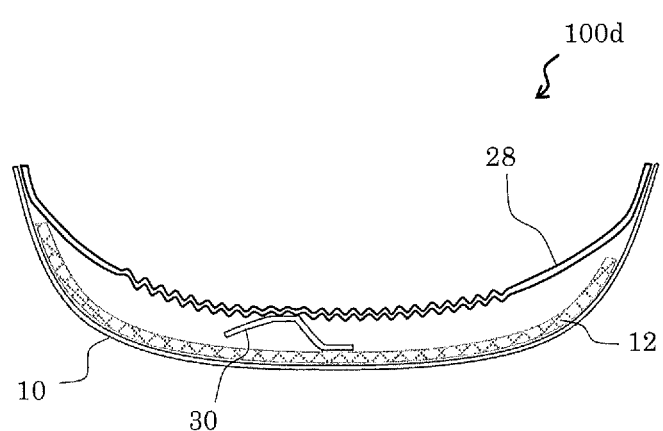

FIG. 6 is a schematic diagram illustrating another example of an absorbent article according to the present invention. FIG. 6(A) is a plan view thereof and FIG. 6(B) is a longitudinal end face view taken along line VIB-VIB shown in FIG. 6(A).

Absorbent article 100d shown in FIG. 6 is basically similar to absorbent article 100, except for skin contact member 28 having a configuration different from that of skin contact member 14.

As shown in FIG. 6, skin contact member 28 has two belt-like members on the right and left sides extending in the front-rear direction. Each of the belt-like members preferably has a lateral direction width of 10-30 mm. The spacing between the two belt-like members (i.e. the spacing between the inner side edge parts) is preferably 20-70 mm when they are used for an infant's absorbent article and is preferably 30-100 mm when they are used for an adult's absorbent article.

As compared to skin contact member 14, which is formed in a sheet, the contact area with respect to the wearer body of skin contact member 28, having two belt-like members, becomes small and, thus, the pressure is higher. Accordingly, the belt-like member is preferably not stimulative to the skin and should preferably be smooth and have high cushioning properties. In order to increase cushioning properties, a belt-like member having high stretchability and a relatively large thickness is preferred.

In particular, for example, foam made of PP or polyurethane having stretchability; an elastic thread-knitted article used in a stretch bandage, etc.; or a laminated sheet of an elastic member such as an elastic net and a non-woven fabric are preferably used.

Connecting unit 30 is a sheet-like member and it couples, at coupling parts 32, to the respective under surfaces of the two belt-like members configuring skin contact member 28 at the parts of skin contact member 28 corresponding to the crotch part of the wearer and connects the two belt-like members to each other.

In addition, the rear end part of connecting unit 30 couples to the top surface of absorber 12.

In this way, the spacing between the under surface of skin contact member 28 and the top surface of absorber 12 can be kept above a certain value. For example, in the case of an infant's absorbent article, the spacing is preferably kept at 10-20 mm.

Accordingly, by means of skin contact member 28 having two belt-like members and connecting unit 30 that connects the two belt-like members to each other, urine permeation opening Of and feces permeation opening Or are respectively formed in the front body and the rear body.

In addition, as shown in FIG. 6(A), the top surface of the part of connecting unit 30 between the two coupling parts 32 is exposed and will be in contact with the crotch part of the wearer at the time of use.

Accordingly, since connecting unit 30 couples skin contact member 28 to absorber 12, skin contact member 28 is substantially incapable of moving in the lateral direction; however, it is movable within a certain range in the front-rear direction. Accordingly, the part of connecting unit 30 which is present between the two belt-like members configuring skin contact member 28 (i.e. the part between urine permeation opening Of and feces permeation opening Or) can be easily made in close attachment with the crotch part (perineal area) of the wearer.

As with connecting unit 16, connecting unit 30 includes a hanging part, which is forward of coupling parts 32. In this way, a smooth transfer of urine to absorber 12 is achieved and this is particularly useful when the absorbent article according to the present invention is intended for females.

Absorbent article 100*d* according to the present invention illustrated in FIG. 6 can be specifically configured in the following manner.

A belt-like member having a width of 20 mm and stretchability and cushioning properties, and which is obtained by, for example, aligning three polyurethane filaments (200 dtex) (manufactured by, for example, Du Pont-Toray Co., Ltd.) in a parallel manner with a spacing of 5 mm between each other and by sandwiching the same, in a stretched condition, between two PE/PP spunbond non-woven fabrics (manufactured by, for example, Chisso Corporation) having a basis weight of 15 g/m$^2$, and then by bonding the same with an adhesive, may be used for skin contact member 28.

Skin contact member 28 is provided by coupling the vicinity of the front end parts and rear end parts of these two belt-like members to leak preventer 10 such that the spacing therebetween is, for example, 40 mm.

Connecting unit 30 may be obtained by laminating a TCF non-woven fabric (manufactured by, for example, Futamura Chemical Co., Ltd.) above the top surface of an elastomer net (35 mesh) (manufactured by, for example, Conwed Global Netting Solutions). Connecting unit 30 is, for example, formed in a belt-shaped and sheeted form having a front-rear direction length of 100 mm and a lateral direction width of 60 mm.

FIG. 7 contains plan views illustrating various arrangement examples of a skin contact member having two belt-like members used for the absorbent article according to the present invention.

In skin contact member 28*a* illustrated in FIG. 7(A), the two belt-like members are arranged in a parallel manner. Spacing Lw between the two belt-like members is, as described above, preferably 20-70 mm when the belt-like members are used for an infant's absorbent article and is preferably 30-100 mm when the belt-like members are used for an adult's absorbent article. Connecting unit 30*a* couples to the two belt-like members at two locations on the right and left sides thereof.

In skin contact member 28*b* illustrated in FIG. 7(B), the two belt-like members are arranged in a crossed manner. Spacing Lw between the two belt-like members is preferably 50-70 mm at the part with the largest spacing when the belt-like members are used for an infant's absorbent article and is preferably 70-100 mm at the part with the largest spacing when the belt-like members are used for an adult's absorbent article. Connecting unit 30*a* couples to the two belt-like members at one location at the central part in the lateral direction.

In skin contact member 28*c* illustrated in FIG. 7(C), the two belt-like members are arranged in a spaced-apart manner and the width between the coupling locations of connecting unit 30*a* is small and it becomes larger when approaching the front end part and also when approaching the rear end part. Spacing Lw between the two belt-like members is preferably 50-70 mm at the part with the largest spacing and is preferably 20-40 mm at the part with the smallest spacing when the belt-like members are used for an infant's absorbent article, and is preferably 70-100 mm at the part with the largest spacing and is preferably 30-50 mm at the part with the smallest spacing when the belt-like members are used for an adult's absorbent article. Connecting unit 30*a* couples to the two belt-like members at two locations on the right and left sides thereof.

FIG. 8 is a schematic diagram illustrating another example of an absorbent article according to the present invention. FIG. 8(A) is a plan view thereof and FIG. 8(B) is a longitudinal end face view taken along line VIIIB-VIIIB shown in FIG. 8(A).

Absorbent article 100*e* shown in FIG. 8 is basically similar to absorbent article 100*d*, except for connecting unit 30*b* having a configuration different from that of connecting unit 30.

Connecting unit 30*b* couples, at two locations on the right and left sides of the front end part thereof, to the under surfaces of parts of the two belt-like members configuring skin contact member 28, which correspond to the crotch part of the wearer. In addition, as will be described below, connecting unit 30*b* also couples to absorber 12 and thus, it is possible to prevent the lateral positional displacement of skin contact member 28 at the time of use. Moreover, skin contact member 28 is movable within a certain range in the front-rear direction.

Further, a greater part of the rear side of connecting unit 30*b* covers, in the rear body, the entire top surface of absorber 12. The coupling between connecting unit 30*b* and absorber 12 may be made, in the part where contact is made therebetween, totally or only partially.

Connecting unit 30*b* receives feces excreted from the wearer and penetrated through feces permeation opening Or.

According to the present embodiment, connecting unit 30*b* is preferably coupled to leak preventer 10 at its right and left edge parts and its back end part. In this way, absorber 12 is present in the enclosed space formed by connecting unit 30*b* and leak preventer 10 in the rear body and thus, when a liquid-impermeable or liquid-poorly-permeating material is used for connecting unit 30*b*, the leakage of urine absorbed by absorber 12 to the outside can be prevented. In addition, it is also possible to eliminate problems such as the odor becoming strong due to the mixing of the feces received at the upper side of connecting unit 30*b* and the urine absorbed in absorber 12 at the under surface of connecting unit 30*b* and the easy occurrence of rashes.

For connecting unit 30*b*, a connecting unit similar to connecting unit 16*a* used in absorbent article 100*a* may be used.

Connecting unit 30*b* is a sheet-like member and it couples, at coupling parts 32*a*, to the respective under surfaces of the two belt-like members configuring skin contact member 28 at the parts of skin contact member 28 corresponding to the crotch part of the wearer and connects the two belt-like members to each other.

In addition, as described above, connecting unit 30*b* couples to the top surface of absorber 12.

In this way, the spacing between the under surface of skin contact member 28 and the top surface of absorber 12 can be kept above a certain value. For example, in the case of an infant's absorbent article, the spacing is preferably kept at 10-20 mm.

Accordingly, by means of skin contact member 28 having two belt-like members and connecting unit 30*b* that connects the two belt-like members to each other, urine permeation opening Of and feces permeation opening Or are respectively formed in the front body and the rear body.

In addition, as shown in FIG. 8(A), the upper side of the part of connecting unit 30*b* between the two coupling parts 32*a* is exposed and will be in contact with the crotch part of the wearer at the time of use.

Accordingly, since connecting unit 30*b* couples skin contact member 28 to absorber 12, skin contact member 28 is substantially incapable of moving in the lateral direction; however, it is movable within a certain range in the front-rear direction. Accordingly, the part of connecting unit 30*b* which is present between the two belt-like members configuring skin contact member 28 (i.e. the part between urine permeation opening Of and feces permeation opening Or) can be easily made in close attachment with the crotch part (perineal area) of the wearer.

FIG. 9 is a schematic diagram illustrating another example of an absorbent article according to the present invention. FIG. 9(A) is a plan view thereof and FIG. 9(B) is a longitudinal end face view taken along line IXB-IXBB shown in FIG. 9(A).

Absorbent article 100f shown in FIG. 9 is basically similar to absorbent article 100d, except for connecting unit 30c having a configuration different from that of connecting unit 30.

Connecting unit 30c couples, at two locations on the right and left sides of the front end part thereof, to the under surfaces of parts of the two belt-like members configuring skin contact member 28, which correspond to the crotch part of the wearer, and the rear end part thereof couples to the top surface of absorber 12, which is located substantially directly beneath the rear end part.

The right and left end parts of connecting unit 30c extend up to the right and left end parts of leak preventer 10, at the central part of absorbent article 100f. In this way, connecting unit 30c divides the internal space of leak preventer 10 into front and rear sections and, thus, it is possible to effectively prevent the urine excreted into the internal space of leak preventer 10 in the front body from transferring into the rear body and the feces excreted into the internal space of leak preventer 10 in the rear body from transferring into the front body. In particular, connecting unit 30c preferably has leakage prevention properties.

Thus, since connecting unit 30c couples skin contact member 28 and absorber 12, skin contact member 28 is substantially incapable of moving in the lateral direction; however, it is movable within a certain range in the front-rear direction. Accordingly, the part of skin contact member 30c which is present between the two belt-like members configuring skin contact member 28 (i.e. the part between urine permeation opening Of and feces permeation opening Or) can be easily made in close attachment with the crotch part (perineal area) of the wearer.

FIG. 10 is a schematic diagram illustrating another example of an absorbent article according to the present invention. FIG. 10(A) is a plan view thereof and FIG. 10(B) is a longitudinal end face view taken along line XB-XB shown in FIG. 10(A).

Absorbent article 100g shown in FIG. 10 is basically similar to absorbent article 100d, except for connecting unit 30d having a configuration different from that of connecting unit 30.

Connecting unit 30d includes connecting member 34 that connects the two belt-like members configuring skin contact member 28 to each other and connecting member 36 that connects connecting member 34 and absorber 12. By means of connecting member 34 and connecting member 36, the parts of the two belt-like members configuring skin contact member 28, which correspond to the crotch part of the wearer, and absorber 12, are coupled to each other.

Thus, since connecting unit 30d couples skin contact member 28 to absorber 12, skin contact member 28 is substantially incapable of moving in the lateral direction; however, it is movable within a certain range in the front-rear direction. Accordingly, the central part of connecting unit 30d that is present between the two belt-like members configuring skin contact member 28 (i.e. the part between urine permeation opening Of and feces permeation opening Or) can be easily made in close attachment with the crotch part (perineal area) of the wearer.

The front-rear direction length of connecting member 34 is preferably 5-20 mm. The lateral direction width is not particularly limited, as long as the two belt-like members configuring skin contact member 28 can be connected to each other; however, it is preferably 40-140 mm. The lateral direction width is more preferably 40-100 mm in the case of an infant's absorbent article. The lateral direction width is more preferably 60-140 mm in the case of an adult's absorbent article.

Connecting member 34 preferably has cushioning properties since it makes contact with the crotch part of the wearer. In order to allow it to have cushioning properties, connecting member 34 preferably makes use of an elastic member and has a certain thickness. For example, a cylinder configured from foam made of PP, polyurethane or the like, a rubber tube, an opened tow or a non-woven laminated body may be used.

FIG. 11 is a schematic perspective view of connecting member 34. In FIG. 11, the cylindrical shape of connecting member 34 is crushed into a flat shape. By assuming such shape, even when contact is made with the crotch part of the wearer, the risk of hurting the skin thereof is reduced.

As shown in FIG. 10, connecting member 34 is bonded to and provided on the top surface side of the central part of skin contact member 28.

For example, polyester type flexible urethane foam (manufactured by, for example, Inoac Corporation) having a front-rear direction length of 20 mm, a lateral direction width of 70 mm and a thickness of 3 mm may be used for connecting member 34.

FIG. 12 is a schematic plan view of connecting member 36. Connecting member 36 illustrated in FIG. 12 has a sheet-like shape.

For example, connecting member 36 has a belt-shaped and sheeted form having a front-rear direction length of 100 mm and a lateral direction width of 30 mm.

Further, for example, connecting member 36 may be obtained by laminating a TCF non-woven fabric (manufactured by, for example, Futamura Chemical Co., Ltd.) above the top surface of an elastomer net (35 mesh) (manufactured by, for example, Conwed Global Netting Solutions).

As shown in FIG. 10, connecting member 36 is provided so as to cover the top surface of the central part of connecting member 34. The part of connecting member 36 which is present forward of connecting member 34 forms a lingui-form hanging part. In this way, a smooth transfer of urine to absorber 12 is achieved and this is particularly useful when the absorbent article according to the present invention is intended for female.

In addition, the rear end part of connecting member 36 is coupled to the top surface of absorber 12.

Accordingly, by means of skin contact member 28, which has two belt-like members, and connecting unit 30d that includes connecting member 34, which connects the two belt-like members to each other, and connecting member 36, urine permeation opening Of and feces permeation opening Or are respectively formed in the front body and the rear body.

In addition, as shown in FIG. 10(A), the upper side of the central part of connecting member 36 of connecting unit 30b is exposed and will be in contact with the crotch part of the wearer at the time of use.

FIG. 13 is a schematic diagram illustrating another example of an absorbent article according to the present invention. FIG. 13(A) is a plan view thereof and FIG. 13(B) is a longitudinal end face view taken along line XIIIB-XIIIB shown in FIG. 13(A).

Absorbent article 100h shown in FIG. 13 is basically similar to absorbent article 100g, except for skin contact member 38 having a configuration different from that of skin contact member 28.

FIG. 14 is a schematic diagram of skin contact member 38. FIG. 14(A) is a side view thereof and FIG. 14(B) is a lateral end face view taken along line XIVB-XIVB shown in FIG. 14(A).

As shown in FIG. 14, skin contact member 38 includes belt-like member 40 and hanging member 42 having one end thereof folded to cover the top surface of belt-like member 40 and the other end thereof hanging down from belt-like member 40.

It should be noted that in an embodiment of the skin contact member, the hanging member may be coupled to the belt-like member at the under surface of the belt-like member.

For example, belt-like member 40 may be configured using the same material as that of the belt-like members configuring skin contact member 28 used in absorbent article 100d.

In particular, for example, a rubber thread band (for example, pajama rubber, manufactured by Fujihato) having a width of 10 mm may be used.

For example, hanging member 42 may be configured using a spunmelt non-woven fabric or the same material as that of skin contact member 14 used in absorbent article 100.

In particular, for example, a PP/SMS non-woven fabric (manufactured by, for example, Avgol) having a basis weight of 15 g/m² may be used.

In FIG. 14, hanging member 42 is pleated; however, a non-pleated hanging member may also be preferably used in the present invention.

The length of the hanging part of hanging member 42 is, for example, 10-30 mm.

The distance between the end part of the hanging part of hanging member 42 in the vicinity of the crotch part and absorber 12 is preferably 1-3 mm; however, both may be partially in contact with each other.

The coupling method of belt-like member 40 and hanging member 42 is not particularly limited; however, examples thereof may include a method of sewing using a sewing machine and a coupling method using an adhesive.

According to absorbent article 100h, skin contact member 38 has two belt-like members 40 on the right and left sides thereof and hanging parts 42 hanging down from the belt-like members 40 and two belt-like members 40 are provided in parallel with each other. The spacing between belt-like members 40 is, for example, 60 mm.

In the conventional absorbent article, there existed a problem in which urine excreted from the wearer easily leaked to the outside of the absorbent article by transferring along the wearer's skin, whereas in the embodiment of the absorbent article according to the present invention, since skin contact member 38 is closely attached to the skin, even when urine transfers along the skin, the flow of urine is stopped by skin contact member 38 and thereafter, urine transfers along hanging member 42 of skin contact member 38 and smoothly moves onto absorber 12.

Connecting unit 30d connects the two belt-like members 40 to each other at the parts of skin contact member 38 corresponding to the crotch part of the wearer. Connecting unit 30d may be directly coupled to belt-like members 40 or may be coupled thereto via hanging members 42.

For connecting unit 30d, a connecting unit similar to the one used in absorbent article 100g may be used.

FIG. 15 is a schematic diagram illustrating another example of an absorbent article according to the present invention. FIG. 15(A) is a plan view thereof and FIG. 15(B) is a longitudinal end face view taken along line XVB-XVB shown in FIG. 15(A).

Absorbent article 100i shown in FIG. 15 is basically similar to absorbent article 100h, except for connecting unit 30e having a configuration different from that of connecting unit 30d.

Connecting unit 30e includes connecting member 34 that connects two skin contact members 38 to each other and connecting member 36a that connects connecting member 34 and absorber 12. By means of connecting member 34 and connecting member 36a, the parts of skin contact members 38 corresponding to the crotch part of the wearer and absorber 12, are coupled to each other.

Thus, since connecting unit 30e couples skin contact members 38 to absorber 12, skin contact members 38 are substantially incapable of moving in the lateral direction; however, they are movable within a certain range in the front-rear direction. Accordingly, the central part of connecting unit 30e that is present between the two skin contact members (i.e. the part between urine permeation opening Of and feces permeation opening Or) can be easily made in close attachment with the crotch part (perineal area) of the wearer.

For connecting member 34 used in connecting unit 30e, a connecting member similar to the one used in connecting unit 30d may be used.

FIG. 16 is a schematic plan view of connecting member 36a.

As shown in FIG. 16, connecting member 36a has a front side part that couples to connecting member 34 and a rear side part that covers absorber 12 in the rear body.

The front side part of connecting member 36a may be similar to connecting member 36 used in absorbent article 100h.

The rear side part of connecting member 36a covers, in the rear body, the entire upper side of absorber 12. The bonding between connecting member 36a and absorber 12 may be made, in the part where contact is made therebetween, totally or only partially.

Connecting unit 36a receives feces excreted from the wearer and penetrated through feces permeation opening Or.

According to the present embodiment, connecting unit 36a preferably couples to leak preventer 10 at its right and left side edge parts and its rear end part. In this way, absorber 12 is present in the enclosed space formed by connecting unit 36a and leak preventer 10, in the rear body, and thus, when a liquid-impermeable or liquid-poorly-permeating material is used for connecting unit 36a, the leakage of urine absorbed by absorber 12 to the outside can be prevented. In addition, it is also possible to eliminate problems such as the odor becoming strong due to the mixing of the feces received at the upper side of connecting unit 36a and the urine absorbed in absorber 12 at the under surface of connecting unit 36a and the easy occurrence of rashes.

The width of the front side part of connecting member 36a is smaller than the spacing between two skin contact members 38 and the front side part hangs downward in the section which is forward of the coupling part with connecting member 34.

The width of the rear side part of connecting member 36a is larger than the lateral direction width of absorber 12.

The front and rear side parts of connecting member 36a may be obtained by partially superimposing thereon and coupling thereto a corresponding sheet having a different width that configures either of them; however, they may alternatively be a unitary member.

For example, a material in which a PE film is laminated above an SMS non-woven fabric may be used for connecting member 36a.

The absorbent article according to the present invention is not particularly limited, as long as it is provided with the leak preventer, absorber, skin contact member and connecting unit, all described above, and for example, various components of the publicly-known conventional absorbent article may be additionally provided.

For example, the absorbent article according to the present invention may be provided with a leg gather.

The leg gather is not particularly limited and, for example, a leg gather similar to the leg gather in the publicly-known conventional absorbent article may be used.

Leg gathers are generally classified into two types. One type is an outer leg gather (also referred to as a "gusset gather." Hereinafter, it will be referred to as an "OLG") which is present on both the right and left side edges of the absorbent article body. The other is an inner leg gather (also referred to as a "standing leg gather." Hereinafter, it will be referred to as an "ILG") which is provided inside the absorbent article and which sterically rises from both sides of the absorber configured from a super absorbent polymer, pulp or the like.

Accordingly, in one of the preferred embodiments of the absorbent article according to the present invention, a pair of right and left inner leg gathers is further provided, further outside from a position where the skin contact member is present in the lateral direction.

Additionally, in another preferred embodiment of the absorbent article according to the present invention, a pair of right and left outer leg gathers is further provided, further outside from a position where the skin contact member is present in the lateral direction.

It should be noted that the manner of providing the ILG and OLG is not particularly limited in the present invention. For example, the ILG may be used alone, the OLG may be used alone, or both the ILG and OLG may be used.

FIG. 17 is a schematic diagram illustrating another example of an absorbent article according to the present invention, FIG. 17(A) is a plan view of an absorbent article in the form of an underpants-type diaper, which is cut along the right and left side parts (denoted with "Z" in the figure) of the waist gather and developed; and FIG. 17(B) is a perspective view thereof.

Absorbent article 100j shown in FIG. 17 is basically similar to absorbent article 100f; however, it differs therefrom with respect to the points that: top sheet 24a is provided above first leak preventer 10 and absorber 12; a pair of right and left outer leg gathers 50 is further provided, further outside from a position where skin contact member 28 is present in the lateral direction; a detachable member is not provided since absorbent article 100j is an underpants-type diaper; and the point that external covering sheet 60 that covers leak preventer 10b and assumes the underpants shape and waist gather 70 that attaches closely around the waist of the wearer at the time of use, are respectively provided.

Leak preventer 10b in absorbent article 100j differs with respect to details such as shape, etc.; however, it corresponds to leak preventer 10 in absorbent article 100f.

Top sheet 24a thoroughly covers first leak preventer 10 and absorber 12. The top sheet is not particularly limited and, for example, any publicly-known conventional top sheet may be used.

Outer leg gather 50 is configured by thread-like rubber that is fixed by being covered by top sheet 24a. For such thread-like rubber, three polyurethane filaments, for example, may be used.

External covering sheet 60 and waist gather 70 are not particularly limited and, for example, any publicly-known conventional external covering sheet and waist gather may be used.

The absorbent article according to the present invention may be in the form of a waist band tape or underpants (i.e. tapeless).

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for paper diapers (for infants and adults), incontinence articles, training pants, or the like.

DESCRIPTION OF THE REFERENCE NUMERALS 10, 10a, 10b Leak preventer
12, 12a Absorber
14, 14a, 14b, 28, 28a, 28b, 28c 38 Skin contact member
16, 16a, 16b, 16c, 30, 30a, 30b, 30c, 30d, 30e Connecting unit
18, 19, 19a, 20, 32, 32a Coupling part
22 Hanging part
24, 24a Top sheet
26 Detachable member
34, 36, 36a Connecting member
40 Belt-like member
42 Hanging member
50 Outer leg gather
60 External covering sheet
70 Waist gather
100, 100a, 100b, 100c, 100d, 100e, 100f, 100g, 100h, 100i, 100j Absorbent article

The invention claimed is:

1. An absorbent article, comprising:
a leak preventer in sheet form;
an absorber that is arranged above the leak preventer and that includes at least one layer capable of absorbing a bodily fluid;
a skin contact member that is arranged above the absorber, between a front part of the leak preventer and a rear part of the leak preventer, the skin contact member being configured to make contact with a wearer's skin and to be spaced apart from the absorber at a time of use; and
a connecting unit that is attached with a part of the skin contact member and with the absorber, the part of the skin contact member being configured to correspond to a crotch part of the wearer at a time of use,
wherein:
a center part of the absorber is aligned with a front part of the connecting unit at a time of use, the front part of the connecting unit is aligned with the part of the skin contact member at a time of use, the connecting unit extends from the part of the skin contact member to the rear part of the leak preventer so that the connecting unit covers a rear part of the absorber and does not cover a front part of the absorber, the front part of the absorber extending from the center part of the absorber to a front end of the absorber, and the skin contact member consists of two separate belt members that are each directly attached to the connecting unit at the part of the skin contact member.

2. The absorbent article according to claim 1, wherein the skin contact member has a urine permeation opening in a front body part and a feces permeation opening in a rear body part.

3. The absorbent article according to claim 2, wherein a part of the connecting unit hangs down to a lower side of the urine permeation opening.

4. The absorbent article according to claim 2, wherein the connecting unit is configured to cover at least part of the absorber in an area from the crotch part of the wearer at a time of use to the rear part of the absorber.

5. The absorbent article according to claim 2, wherein right and left end parts of the connecting unit extend to right and left end parts of the leak preventer.

6. The absorbent article according to claim 1, wherein the two separate belt members extend in a front-rear direction.

7. The absorbent article according to claim 6, wherein a part of the connecting unit hangs down to a lower side of the urine permeation opening.

8. The absorbent article according to claim 6, wherein the connecting unit is configured to cover at least part of the absorber in an area from the crotch part of the wearer at a time of use to the rear part of the absorber.

9. The absorbent article according to claim 6, wherein right and left end parts of the connecting unit extend to right and left end parts of the leak preventer.

10. The absorbent article according to claim 1, wherein:
the two separate belt members extend in a front-rear direction, and
the skin contact member includes a hanging member that hangs down from the two belt members.

11. The absorbent article according to claim 10, wherein a part of the connecting unit hangs down to a lower side of the urine permeation opening.

12. The absorbent article according to claim 10, wherein the connecting unit is configured to cover at least part of the absorber in an area from the crotch part of the wearer at a time of use to the rear part of the absorber.

13. The absorbent article according to claim 10, wherein right and left end parts of the connecting unit extend to right and left end parts of the leak preventer.

14. The absorbent article according to claim 1, wherein the absorber contains a super absorbent polymer.

15. The absorbent article according to claim 1, further comprising a pair of right and left inner leg gathers provided further outside from a position where the skin contact member is present in a lateral direction.

16. The absorbent article according to claim 1, further comprising a pair of right and left outer leg gathers provided further outside from a position where the skin contact member is present in a lateral direction.

17. The absorbent article according to claim 1, wherein a forward-most part of the connecting unit hangs down to a lower side of the urine permeation opening, the forward-most part of the connecting unit being forward of the front part of the connecting unit that is aligned with the part of the skin contact member at a time of use.

18. The absorbent article according to claim 1, wherein the two separate belt members are spaced apart from each other at the location of their direct attachment with the connecting unit.

19. The absorbent article according to claim 1, wherein the two separate belt members are spaced apart from each other along their entire lengths.

20. An absorbent article, comprising:
a leak preventer in sheet form;
an absorber that is arranged above the leak preventer and that includes at least one layer capable of absorbing a bodily fluid;
a skin contact member that is arranged above the absorber, between a front part of the leak preventer and a rear part of the leak preventer, the skin contact member being configured to make contact with a wearer's skin and to be spaced apart from the absorber at a time of use;
a connecting unit that is attached with a part of the skin contact member and with the absorber, the part of the skin contact member being configured to correspond to a crotch part of the wearer at a time of use;
and a pair of right and left leg gathers,
wherein:
a center part of the absorber is aligned with a front part of the connecting unit at a time of use,
the front part of the connecting unit is aligned with the part of the skin contact member at a time of use,
the connecting unit extends from the part of the skin contact member to the rear part of the leak preventer so that the connecting unit covers a rear part of the absorber and does not cover a front part of the absorber, the front part of the absorber extending from the center part of the absorber to a front end of the absorber,
the skin contact member consists of two separate belt members that are each directly attached to the connecting unit at the part of the skin contact member, and
the two belt members are not directly attached to the pair of left and right leg gathers.

* * * * *